US00PP29247P2

(12) United States Plant Patent
Beekenkamp

(10) Patent No.: US PP29,247 P2
(45) Date of Patent: Apr. 17, 2018

(54) ***BEGONIA* PLANT NAMED 'BKPBEEAS'**

(50) Latin Name: *Begonia×hiemalis*
Varietal Denomination: Bkpbeeas

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 15/530,376

(22) Filed: Jan. 4, 2017

(51) Int. Cl.
*A01H 5/02* (2006.01)

(52) U.S. Cl.
USPC ..... Plt./347

(58) Field of Classification Search
USPC ..... Plt./347
See application file for complete search history.

*Primary Examiner* — Annette H Para
(74) *Attorney, Agent, or Firm* — C. A. Whealy

(57) ABSTRACT

A new and distinct cultivar of *Begonia* plant named 'Bkpbeeas', characterized by its broadly upright to outwardly spreading and mounded plant habit; sturdy plants with freely basal branching habit; dark green-colored leaves; uniform and freely flowering habit; and double flowers that are orange red in color.

2 Drawing Sheets

Botanical designation: *Begonia×hiemalis*.
Cultivar denomination: 'BKPBEEAS'.

BACKGROUND OF THE INVENTION

The present invention relates to a new and distinct cultivar of *Begonia* plant, botanically known as *Begonia×hiemalis*, commercially referred to as Elatior *Begonia* and hereinafter referred to by the name 'Bkpbeeas'.

The new *Begonia* plant is a product of a planned breeding program conducted by the Inventor in Maasdijk, The Netherlands. The objective of the breeding program was to develop new freely branching and freely flowering *Begonia* plants with attractive flowers.

The new *Begonia* plant is a naturally-occurring whole plant mutation of *Begonia×hiemalis* 'Dark Britt', not patented. The new *Begonia* plant was discovered and selected by the Inventor as a single flowering plant from within a population of plants of 'Dark Britt' in a controlled greenhouse environment in Maasdijk, The Netherlands in April, 2012.

Asexual reproduction of the new *Begonia* plant by vegetative tip cuttings in a controlled greenhouse environment in Maasdijk, The Netherlands since January, 2013 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Bkpbeeas'. These characteristics in combination distinguish 'Bkpbeeas' as a new and distinct *Begonia* plant:

1. Broadly upright to outwardly spreading and mounded plant habit.
2. Sturdy plants with freely basal branching habit.
3. Dark green-colored leaves.
4. Uniform and freely flowering habit.
5. Double flowers that are orange red in color.

Plants of the new *Begonia* can be compared to plants of the mutation parent, 'Dark Britt'. Plants of the new *Begonia* differ primarily from plants of 'Dark Britt' in the following characteristics:

1. Plants of the new *Begonia* are more compact than plants of 'Dark Britt'.
2. Plants of the new *Begonia* and 'Dark Britt' differ in flower color as plants of 'Dark Britt' have bright orange-colored flowers.

Plants of the new *Begonia* can be compared to plants of *Begonia×hiemalis* 'Reina', disclosed in U.S. Plant Pat. No. 19,336. Plants of the new *Begonia* differ primarily from plants of 'Reina' in the following characteristics:

1. Plants of the new *Begonia* are more compact than plants of 'Reina'.
2. Plants of the new *Begonia* and 'Reina' differ in flower color as plants of 'Reina' have dark orange-colored flowers.

Plants of the new *Begonia* can also be compared to plants of *Begonia×hiemalis* 'Batik', not patented. Plants of the new *Begonia* differ primarily from plants of 'Batik' in the following characteristics:

1. Flowers of plants of the new *Begonia* are double in form whereas flowers of plants of 'Batik' are semi-double in form.
2. Plants of the new *Begonia* and 'Batik' differ in flower color as plants of 'Batik' have bright orange-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'Bkpbeeas' grown in a container.

The photograph on the second sheet are close-up views of upper and lower surfaces of typical developed flowers and leaves of 'Bkpbeeas'.

DETAILED BOTANICAL DESCRIPTION

Plants used for the aforementioned photographs and following observations and measurements were grown during the autumn in 12-cm containers in a glass-covered greenhouse in Maasdijk, The Netherlands. During the production of the plants, day and night temperatures ranged from 19° to 21° C. Plants were twelve weeks old when the photographs and the description were taken. In the following description, color references are made to The Royal Horticultural Society Colour Chart, 2015 Edition, except where general terms of ordinary dictionary significance are used.

Botanical classification: *Begonia×hiemalis* 'Bkpbeeas'.

Parentage: Naturally-occurring whole plant mutation of *Begonia hiemalis* 'Dark Britt', not patented.

Propagation:

*Type*.—By vegetative tip cuttings.

*Time to initiate roots*.—About 20 days at temperatures about 25° C.

*Time to produce a rooted young plant*.—About 35 to 36 days at temperatures about 21° C. to 23° C.

*Root description*.—Fine, fibrous; typically brown in color, actual color of the roots is dependent on substrate composition, water quality, fertilizer type and formulation, substrate temperature and physiological age of roots; plants of the new *Begonia* have not been observed to form tubers.

*Rooting habit*.—Freely branching habit; dense.

Plant description:

*Plant and growth habit*.—Broadly upright to outwardly spreading and mounded plant habit; plant shape, broadly ovate; moderately vigorous growth habit; moderate growth rate.

*Plant height, soil level to top of foliar plane*.—About 19.3 cm.

*Plant height, soil level to top of floral plane*.—About 22.3 cm.

*Plant width*.—About 25.9 cm.

*Lateral branch description*.—Branching habit: Freely branching habit with about two basal branches developing per plant; each basal branch with about seven lateral branches; pinching is not required. Length: About 8 cm. Diameter: About 9 mm. Internode length: About 2.5 cm. Strength: Moderately strong. Aspect: About 40° from vertical. Texture and luster: Smooth, glabrous; glossy. Color, developing: Close to 146D. Color, fully developed: Close to 146C.

*Leaf description*.—Arrangement: Alternate, simple. Length: About 11.4 cm. Width: About 9.4 cm. Shape: Ovate. Apex: Acute. Base: Oblique, lobes meeting to slightly imbricate. Margin: Crenate to dentate; strongly undulate. Texture and luster, upper surface: Smooth, glabrous; slightly velvety; slightly glossy. Texture and luster, lower surface: Sparsely pubescent along veins; moderately glossy. Venation pattern: Laciniate. Color: Developing leaves, upper surface: Close to 143A. Developing leaves, lower surface: Close to 147C. Fully expanded leaves, upper surface: Darker than between 147A and N189A; venation, close to 143B and 143C. Fully expanded leaves, lower surface: Close to between 148B and 191A; venation, close to 144B and 144C. Petioles: Length: About 4.9 cm. Diameter: About 6 mm. Texture and luster, upper and lower surfaces: Sparsely pubescent; moderately glossy. Color, upper surface: Close to 146D and 173A to 173B. Color, lower surface: Close to 145A and N170B. Stipules: Quantity per leaf: Two. Length: About 1.3 cm. Width: About 1.3 cm. Shape: Deltoid. Apex: Acute. Base: Broadly cuneate. Margins: Entire. Color, upper and lower surfaces: Close to 145B to 145C.

Flower description:

*Flowering habit*.—Rotate double sterile flowers arranged in axillary compound cymes; freely flowering habit with about nine flowers per cyme and about 500 flowers developing per plant during the flowering season; flowers face upright to slightly outwardly.

*Fragrance*.—None detected.

*Natural flowering season*.—Long flowering period, plants flower freely and continuously from spring into the autumn in The Netherlands; during the winter in a greenhouse, plants begin flowering about 50 days after exposure to photoinductive treatments.

*Postproduction longevity*.—Individual flowers last about ten days on the plant; flowers not persistent; plants maintain good substance for about 20 to 30 days in an interior environment.

*Inflorescence height*.—About 7.2 cm.

*Inflorescence diameter*.—About 8.1 cm.

*Flower buds*.—Length: About 1.5 cm. Diameter, flattened: About 1.3 cm. Shape: Broadly obovate; flattened. Texture and luster: Smooth, glabrous, slightly velvety; very slightly glossy. Color: Close to 150D; distally, close to 29B.

*Flowers*.—Diameter: About 4.7 cm. Depth: About 2.3 cm. Tepals: Quantity and arrangement: Four per flower arranged in two whorls. Length, lower tepals: About 3 cm. Width, lower tepals: About 4 cm. Length, upper tepals: About 2 cm. Width, upper tepals: About 2.8 cm. Shape: Roughly reniform. Apex: Rounded. Base: Reniform. Margin: Entire; slightly undulate. Texture and luster, upper surface: Smooth, glabrous, moderately velvety; matte. Texture and luster, lower surface: Smooth, glabrous, slightly velvety; matte to very slightly glossy. Color: When opening, upper surface: Close to 30C to 30D; towards the base, close to 154C to 154D. When opening, lower surface: Close to 33C to 33D; towards the base, close to 154D. Fully opened, upper surface: Close to 30A to 30B; towards the base, close to between 154D and 1D; color does not fade with development. Fully opened, lower surface: Close to 33C to 33D; towards the base, close to 154D; color does not fade with development. Tepaloids: Quantity and arrangement: About 30 arranged in multiple whorls at the center of the flower. Length: About 7 mm to 19 mm. Width: About 9 mm to 20 mm. Shape:

Obovate. Apex: Rounded to shallowly cleft. Base: Attenuate. Margin: Entire; very slightly undulate. Texture and luster, upper surface: Smooth, glabrous, moderately velvety; matte. Texture and luster, lower surface: Smooth, glabrous, slightly velvety; matte. Color: When opening, upper surface: Close to 25C; towards the base, close to 1B. When opening, lower surface: Close to 154D; towards the apex and base, strongly tinged with close to 29A. Fully opened, upper surface: Close to 31C; margins, close to 25C; towards the base, close to 2C; color does not fade with development. Fully opened, lower surface: Close to 31C to 31D; towards the base, close to 1C; color does not fade with development.

*Peduncles*.—Length: About 6.9 cm. Diameter: About 5 mm to 6.5 mm. Angle: About 30° from lateral branch axis. Strength: Moderately strong; flexible. Texture and luster: Smooth, glabrous; moderately glossy. Color: Close to 146C to 146D.

*Pedicels*.—Length: About 3 cm. Diameter: About 3 mm. Angle: About 15° from the peduncle axis. Strength: Moderately strong; flexible. Texture and luster: Glabrous; glossy. Color: Close to 145A.

*Flower bracts*.—Quantity and arrangement: Two per flower, opposite. Length: About 1.4 cm. Width: About 1.5 cm. Shape: Roughly orbicular. Apex: Rounded. Margin: Entire. Texture and luster, upper and lower surfaces: Smooth, glabrous; matte. Color, upper and lower surfaces: Close to 143C.

*Reproductive organs*.—None observed, all structures transformed into tepaloids.

*Seeds and fruits*.—Seed and fruit development have not been observed on plants of the new *Begonia* as flowers are sterile.

Pathogen & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'Bkpbeeas' as illustrated and described.

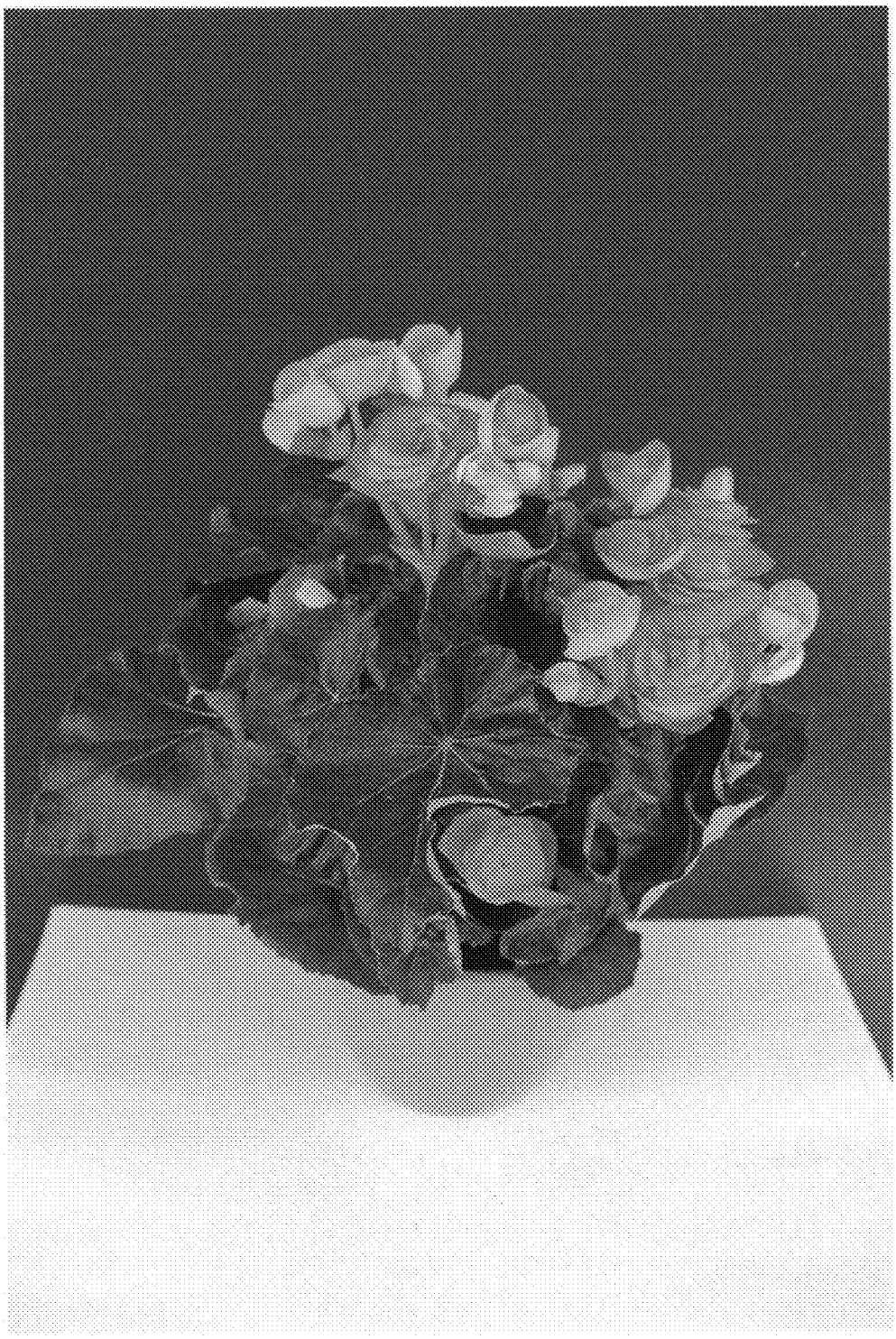

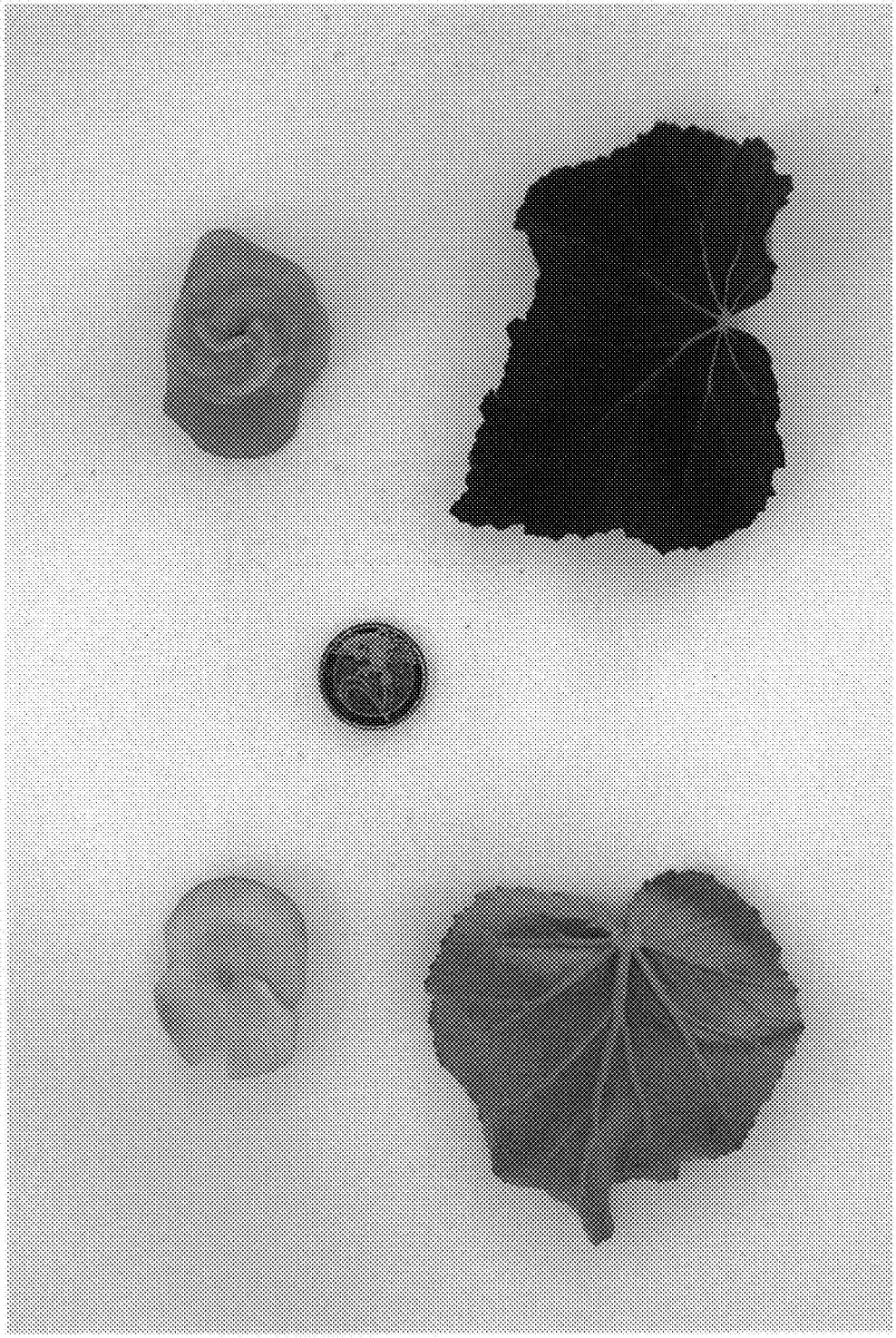

* * * * *